United States Patent
Zheng et al.

(10) Patent No.: US 11,380,937 B2
(45) Date of Patent: Jul. 5, 2022

(54) NON-AQUEOUS ELECTROLYTE FOR LITHIUM ION BATTERY AND LITHIUM ION BATTERY

(71) Applicant: SHENZHEN CAPCHEM TECHNOLOGY CO., LTD., Guangdong (CN)

(72) Inventors: Zhongtian Zheng, Guangdong (CN); Ling Zhong, Guangdong (CN); Shiguang Hu, Guangdong (CN); Qiao Shi, Guangdong (CN); Changchun Chen, Guangdong (CN); Zhaohui Deng, Guangdong (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 333 days.

(21) Appl. No.: 16/632,862

(22) PCT Filed: Dec. 28, 2017

(86) PCT No.: PCT/CN2017/119264
§ 371 (c)(1),
(2) Date: Jan. 21, 2020

(87) PCT Pub. No.: WO2019/024408
PCT Pub. Date: Feb. 7, 2019

(65) Prior Publication Data
US 2020/0168953 A1    May 28, 2020

(30) Foreign Application Priority Data
Jul. 31, 2017 (CN) .......................... 201710640464.2

(51) Int. Cl.
| | |
|---|---|
| *H01M 10/0567* | (2010.01) |
| *H01M 10/0525* | (2010.01) |
| *H01M 10/0568* | (2010.01) |
| *H01M 10/0569* | (2010.01) |
| *C07D 317/36* | (2006.01) |

(52) U.S. Cl.
CPC ...... *H01M 10/0567* (2013.01); *C07D 317/36* (2013.01); *H01M 10/0525* (2013.01); *H01M 10/0568* (2013.01); *H01M 10/0569* (2013.01); *H01M 2300/0025* (2013.01)

(58) Field of Classification Search
CPC ............. H01M 10/05; H01M 10/0567; H01M 10/0568; H01M 10/0569; H01M 10/0525
See application file for complete search history.

(56) References Cited

U.S. PATENT DOCUMENTS

| | | | |
|---|---|---|---|
| 3,663,569 A | 5/1972 | Lew | |
| 6,174,629 B1 | 1/2001 | Gan et al. | |
| 2009/0214938 A1* | 8/2009 | Yamamoto | ............ H01M 4/364 429/94 |
| 2015/0249268 A1* | 9/2015 | Hong | ................ H01M 10/0568 429/188 |

FOREIGN PATENT DOCUMENTS

| | | |
|---|---|---|
| CN | 1495959 A | 5/2004 |
| CN | 102195076 A | 9/2011 |
| CN | 103151559 A | 6/2013 |
| CN | 103354962 A | 10/2013 |
| CN | 103441304 A | 12/2013 |
| CN | 103460496 A | 12/2013 |
| CN | 103594729 A | 2/2014 |
| CN | 104300174 A | 1/2015 |
| CN | 105051965 A | 11/2015 |
| CN | 105161763 A | 12/2015 |
| CN | 105580189 A | 5/2016 |
| CN | 105633461 A | 6/2016 |
| CN | 105830270 A | 8/2016 |
| CN | 106058317 A | 10/2016 |
| CN | 106252639 A | 12/2016 |
| CN | 106328996 A | 1/2017 |

(Continued)

OTHER PUBLICATIONS

Libo Hu et al., Fluorinated electrolytes for 5-V Li-ion chemistry: Dramatic enhancement of LiNi0.5Mn1.5O4/graphite cell performance by a lithium reservoir, Electrochemistry Communications, Apr. 2014, vol. 44, pp. 34-37.

*Primary Examiner* — Kenneth J Douyette

(57) ABSTRACT

Provide is a non-aqueous electrolyte for lithium ion battery, comprising a compound represented by structural formula I:

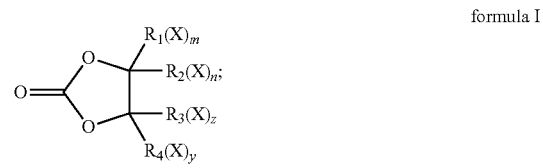

formula I

In formula I, $R_1$, $R_2$, $R_3$ and $R_4$ are each independently selected from hydrogen atom, fluorine atom, cyano group, hydrocarbyl group or halogenated hydrocarbyl group having 1-5 carbon atoms, oxygen-containing hydrocarbyl group having 1-5 carbon atoms, silicon-containing hydrocarbyl group having 1-5 carbon atoms, X is a $-O-R_5-CN$ group, $R_5$ is a hydrocarbyl group or a halogenated hydrocarbyl group having 1-5 carbon atoms, m, n, z and y are integers of 0 or 1, and $m+n+y+z \neq 0$. When the non-aqueous electrolyte is used for lithium ion battery, the decomposition of electrolyte on the surface of electrode can be inhibited, and the high-temperature storage performance is improved with less gas generation and small expansion rate, therefore the high-temperature cycle performance and high-temperature storage performance of the battery are effectively improved.

11 Claims, No Drawings

(56) References Cited

FOREIGN PATENT DOCUMENTS

| | | |
|---|---|---|
| CN | 106410272 A | 2/2017 |
| GB | 1147540 A | 4/1969 |
| JP | 2000123867 A | 4/2000 |
| JP | 2000260467 A | 9/2000 |
| JP | 2006219406 A | 8/2006 |
| JP | 2014182951 A | 9/2014 |
| JP | 2014525667 A | 9/2014 |
| JP | 2015092476 A | 5/2015 |
| WO | 2016025589 A1 | 2/2016 |
| WO | 2016151983 A1 | 9/2016 |

\* cited by examiner

NON-AQUEOUS ELECTROLYTE FOR LITHIUM ION BATTERY AND LITHIUM ION BATTERY

TECHNICAL FIELD

The invention belongs to the technical filed of lithium ion battery electrolyte, in particular to a non-aqueous electrolyte for lithium ion battery and lithium ion battery

BACKGROUND

Lithium ion battery has made great progress in the field of portable electronic products because of its high working voltage, high safety, long service life and no memory effect. Especially with the development of new energy vehicles, lithium ion batteries have shown great application prospects in power supply systems for new energy vehicles.

In non-aqueous electrolyte lithium ion battery, non-aqueous electrolyte is the key factor affecting the high and low temperature performances of the battery. In particular, additives in non-aqueous electrolyte are particularly important for the performances of the battery at high and low temperatures. During the initial charging process of the lithium ion battery, lithium ions in the positive electrode material of the battery are released and embedded into the carbon negative electrode through electrolyte. Due to its high reactivity, the electrolyte reacts on the surface of the carbon negative electrode to produce compounds such as $Li_2CO_3$, LiO, LiOH, etc., thus forming a passivation film on the surface of the negative electrode, which is called solid electrolyte interface film (SEI). The SEI film formed during the initial charging process not only prevents the electrolyte from further decomposing on the surface of the carbon negative electrode, but also acts as a lithium ion channel, allowing only lithium ions to pass through. Therefore, the quality of SEI film determines the performances of lithium ion battery.

In order to improve the various performances of lithium ion batteries, many researchers have tried to improve the quality of SEI films by adding different negative film-forming additives (such as vinylene carbonate, fluoroethylene carbonate and vinylethylene carbonate) to the electrolyte, to improve the various performances of the batteries.

For example, Japanese Patent Laid-Open No. 2000-123867 proposes to improve battery performances by adding vinylene carbonate to the electrolyte. Vinylene carbonate can undergo a reduction decomposition reaction on the surface of the negative electrode prior to solvent molecules, can form a passivation film on the surface of the negative electrode, and prevents electrolyte from further decomposing on the surface of the electrode, thereby improving the cycle performance of the battery. However, after the addition of vinylene carbonate, the battery is prone to generate gas at high-temperature storage, causing the battery to expand.

In addition, the passivation film formed from vinylene carbonate has a large impedance, especially at low temperature, which is prone to precipitate lithium during low-temperature charging and affects the safety of the battery. Fluoroethylene carbonate can also form a passivation film on the surface of the negative electrode to improve the cycle performance of the battery, and the formed passivation film has relatively low impedance and can improve the low-temperature discharge performance of the battery. However, fluoroethylene carbonate produces more gas when stored at high temperature, which obviously reduces the high-temperature storage performance of the battery.

Therefore, it is necessary to conduct more in-depth research on the existing non-aqueous electrolyte and develop a new non-aqueous electrolyte that is conducive to improving the performances of lithium ion battery.

SUMMARY

The application provides a non-aqueous electrolyte for lithium ion battery, aims to solve problems such as gas generation at high-temperature storage and insufficient high-temperature cycle performance for the existing lithium ion battery electrolyte.

In order to achieve the above purpose, the application adopts the following technical solution: A non-aqueous electrolyte for lithium ion battery, comprising a compound represented by structural formula I:

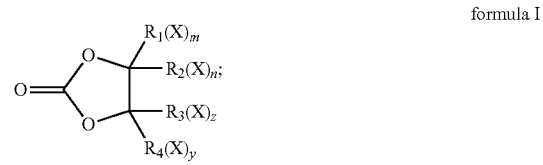

formula I

In formula I, $R_1$, $R_2$, $R_3$ and $R_4$ are each independently selected from hydrogen atom, fluorine atom, cyano group, hydrocarbyl group or halogenated hydrocarbyl group having 1-5 carbon atoms, oxygen-containing hydrocarbyl group having 1-5 carbon atoms, silicon-containing hydrocarbyl group having 1-5 carbon atoms, X is a —O—$R_5$—CN group, $R_5$ is a hydrocarbyl group or a halogenated hydrocarbyl group having 1-5 carbon atoms, m, n, z and y are integers of 0 or 1, and m+n+y+z≠0.

Preferably, $R_1$, $R_2$, $R_3$ and $R_4$ are each independently selected from one of hydrogen atom, fluorine atom, cyano group, methyl group, ethyl group, propyl group, butyl group, fluorinated methyl group, fluorinated ethyl group, fluorinated propyl group, fluorinated butyl group, methylene group, ethylidene group, propylidene group, butylidene group, fluorinated methylene group, fluorinated ethylidene group, fluorinated propylidene group, and fluorinated butylidene group. Preferably, the compound represented by formula I is selected from:

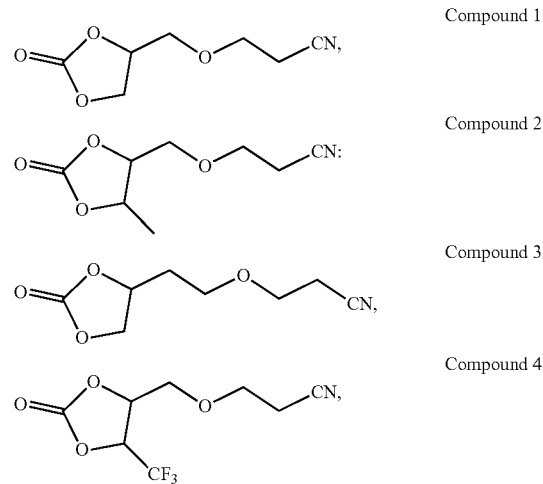

Compound 5

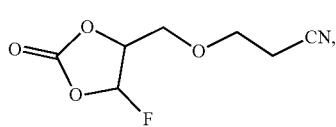

Compound 6

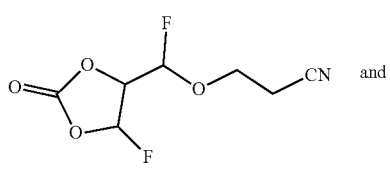
and

Compound 7

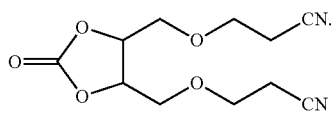

Preferably, the percentage mass content of the compound represented by structural formula I is 0.1% to 10.0% based on the total mass of the non-aqueous electrolyte for lithium ion battery being 100%.

Preferably, the non-aqueous electrolyte for lithium ion battery further comprises at least one of unsaturated cyclic carbonate, fluorinated cyclic carbonate, cyclic sultones, cyclic sulfate, and nitriles.

Preferably, the unsaturated cyclic carbonate is at least one selected from vinylene carbonate (VC), vinylethylene carbonate (VEC), and methylene vinyl carbonate;

the fluorinated cyclic carbonate is at least one selected from fluoroethylene carbonate (FEC), trifluoromethyl vinyl carbonate and difluoroethylene carbonate;

the cyclic sultones is at least one selected from 1,3-propane sultone, 1,4-butane sultone and propenyl-1,3-sultone;

the cyclic sulfate is at least one selected from ethylene sulfate (DTD) and 4-methyl vinyl sulfate;

the nitriles are selected from at least one of succinonitrile (SN), adiponitrile (ADN), 1,2-bis (2-cyanoethoxy) ethane, 1,4-dicyano-2-butene, hexane-1,3,6-tricarbonitrile, and 1,2,3-tris (2-cyanoethoxy) propane.

Preferably, based on the total mass of the non-aqueous electrolyte for lithium ion battery being 100%, the percentage mass content of the unsaturated cyclic carbonate is 0.1-5%; the percentage mass content of the fluorinated cyclic carbonate is 0.1-80%; the percentage mass content of the cyclic sultones is 0.1-5%; the percentage mass content of the cyclic sulfate is 0.1-5%; the percentage mass content of the nitriles is 0.1-5%.

Preferably, the non-aqueous electrolyte for lithium ion battery comprises a solvent and a lithium salt;
the solvent comprises at least one of cyclic carbonate, chain carbonate, fluorine-containing chain carbonate, carboxylic acid ester, fluorine-containing carboxylic acid ester and fluorine-containing aromatic hydrocarbon; the cyclic carbonate is selected from at least one of ethylene carbonate, propylene carbonate and butylene carbonate; the chain carbonate is selected from at least one of dimethyl carbonate, diethyl carbonate, methyl ethyl carbonate and methyl propyl carbonate; the carboxylic acid ester is selected from at least one of methyl acetate, ethyl acetate, propyl acetate, methyl propionate, ethyl propionate and propyl propionate; the fluorine-containing aromatic hydrocarbon is selected from at least one of benzene compounds substituted with one or more fluorines;

the lithium salt is selected from at least one of $LiPF_6$, $LiBF_4$, $LiN(SO_2CF_3)_2$, $LiN(SO_2C_2F_5)_2$, $LiC(SO_2CF_3)_3$ and $LiN(SO_2F)_2$.

The non-aqueous electrolyte for lithium ion battery provided by the application contains a compound represented by formula I. When the non-aqueous electrolyte is used for lithium ion battery, the compound represented by structural formula I can undergo a reduction decomposition reaction prior to solvent molecules in the first charging process, and the reaction product forms a passivation film on the surface of the electrode, and the passivation film can inhibit further decomposition of solvent molecules and lithium salts. In addition, the compound represented by structural formula I can be complexed with high-valence metal ions on the surface of the positive electrode material, thus improving the stability of the surface of the positive electrode material and inhibiting the oxidative decomposition of electrolyte on the surface of the positive electrode, thereby greatly improving the high-temperature storage and high-temperature cycle performances of the battery.

Accordingly, another object of the present application is to provide a lithium ion battery comparing the above-mentioned non-aqueous electrolyte for lithium ion battery.

A lithium ion battery, comprising a positive electrode, a negative electrode, a separator for separating the positive electrode and the negative electrode, and an electrolyte, wherein the electrolyte is the non-aqueous electrolyte as described above.

Preferably, the positive electrode comprises a positive electrode active material, and the active material of the positive electrode is at least one of $LiNi_xCo_yMn_zL_{(1-x-y-z)}O_2$, $LiCo_xL_{(1-x')}O_2$, $LiNi_{x''}L'_{y'}Mn_{(2-x''-y')}O_4$ and $Li_z'MPO_4$, wherein, L is at least one of Al, Sr, Mg, Ti, Ca, Zr, Zn, Si or Fe, $0 \le x \le 1$, $0 \le y \le 1$, $0 \le z \le 1$, $0 < x+y+z \le 1$, $0 < x' \le 1$, $0.3 \le x'' \le 0.6$, $0.01 \le y' \le 0.2$, L' is at least one of Co, Al, Sr, Mg, Ti, Ca, Zr, Zn, Si and Fe; $0.5 \le z' \le 1$, M is at least one of Fe, Mn and Co.

Because of the use of the non-aqueous electrolyte, the lithium ion battery provided by the application can inhibit the decomposition of the electrolyte on the surfaces of positive and negative electrode materials, the performances of the lithium ion battery are greatly improved.

DETAILED DESCRIPTION OF DISCLOSED EMBODIMENTS

In order to make the to-be-solved technical problems, technical solutions and beneficial effects of the present application clearer, the present application will be described in further detail below with reference to embodiments. It should be understood that the specific embodiments described herein are only for the purpose of explaining the present application and are not intended to limit the present application.

The embodiment of the application provides a non-aqueous electrolyte for lithium ion battery, comprising a compound represented by structural formula I:

formula I

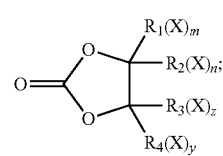

In formula I, $R_1$, $R_2$, $R_3$ and $R_4$ are each independently selected from hydrogen atom, fluorine atom, cyano group, hydrocarbyl group or halogenated hydrocarbyl group having 1-5 carbon atoms, oxygen-containing hydrocarbyl group having 1-5 carbon atoms, silicon-containing hydrocarbyl group having 1-5 carbon atoms, X is a —O—$R_5$—CN group, $R_5$ is a hydrocarbyl group or a halogenated hydrocarbyl group having 1-5 carbon atoms, m, n, z and y are integers of 0 or 1, and m+n+y+z≠0.

Preferably, $R_1$, $R_2$, $R_3$ and $R_4$ are each independently selected from one of hydrogen atom, fluorine atom, cyano group, methyl group, ethyl group, propyl group, butyl group, fluorinated methyl group, fluorinated ethyl group, fluorinated propyl group, fluorinated butyl group, methylene group, ethylidene group, propylidene group, butylidene group, fluorinated methylene group, fluorinated ethylidene group, fluorinated propylidene group, and fluorinated butylidene group. Preferably, fluorinated methyl group, fluorinated ethyl group, fluorinated propyl group, fluorinated butyl methylene group, ethylidene group and ropylidene group each preferably contain three fluorine atoms.

Those skilled in the art can understand that when m is 0, $R_1$ is selected from hydrogen atom, fluorine atom, cyano group, methyl group, ethyl group, propyl group, butyl group, fluorinated methyl group, fluorinated ethyl group, fluorinated propyl group, fluorinated butyl group; When m is 1, $R_1$ cannot be hydrogen atom, fluorine atom, cyano group, or alkyl group, etc., but is an alkylene group corresponding to alkyl group. Therefore, in the present application, when m is 1, $R_1$ is selected from methylene group, ethylidene group, propylidene group, butylidene group, fluorinated methylene group, fluorinated ethylidene group, fluorinated propylidene group, and fluorinated butylidene group; Similarly, when n, z or y is 0, $R_2$, $R_3$ and $R_4$ corresponding thereto are selected from hydrogen atom, fluorine atom, cyano group, methyl group, ethyl group, propyl group, butyl group, fluorinated methyl group, fluorinated ethyl group, fluorinated propyl group, fluorinated butyl group; When n, z or y is 1, $R_2$, $R_3$ and $R_4$ are selected from methylene group, ethylidene group, propylidene group, butylidene group, fluorinated methylene group, fluorinated ethylidene group, fluorinated propylidene group, and fluorinated butylidene group. It should be noted that whether m is 0 or 1 will only change the group represented by $R_1$, and will not change the group represented by $R_2$, $R_3$ and $R_4$. Similarly, as m above, whether n, z or y is 0 or 1 has a similar effect on other groups. That is, when n is 0, $R_2$ is selected from hydrogen atom, fluorine atom, cyano group, methyl group, ethyl group, propyl group, butyl group, fluorinated methyl group, fluorinated ethyl group, fluorinated propyl group, fluorinated butyl group; That is, when n is 1, $R_2$ is selected from methylene group, ethylidene group, propylidene group, butylidene group, fluorinated methylene group, fluorinated ethylidene group, fluorinated propylidene group, and fluorinated butylidene group. When x is 0, $R_3$ is selected from hydrogen atom, fluorine atom, cyano group, methyl group, ethyl group, propyl group, butyl group, fluorinated methyl group, fluorinated ethyl group, fluorinated propyl group, fluorinated butyl group; when x is 1, $R_3$ is selected from methylene group, ethylidene group, propylidene group, butylidene group, fluorinated methylene group, fluorinated ethylidene group, fluorinated propylidene group, and fluorinated butylidene group. When y is 0, $R_4$ is selected from hydrogen atom, fluorine atom, cyano group, methyl group, ethyl group, propyl group, butyl group, fluorinated methyl group, fluorinated ethyl group, fluorinated propyl group, fluorinated butyl group; when y is 1, $R_4$ is selected from methylene group, ethylidene group, propylidene group, butylidene group, fluorinated methylene group, fluorinated ethylidene group, fluorinated propylidene group, and fluorinated butylidene group.

Preferably, the percentage mass content of the compound represented by structural formula I is 0.1% to 10.0% based on the total mass of the non-aqueous electrolyte for lithium ion battery being 100%.

Specifically, the compound represented by structural formula I can be represented as follows:

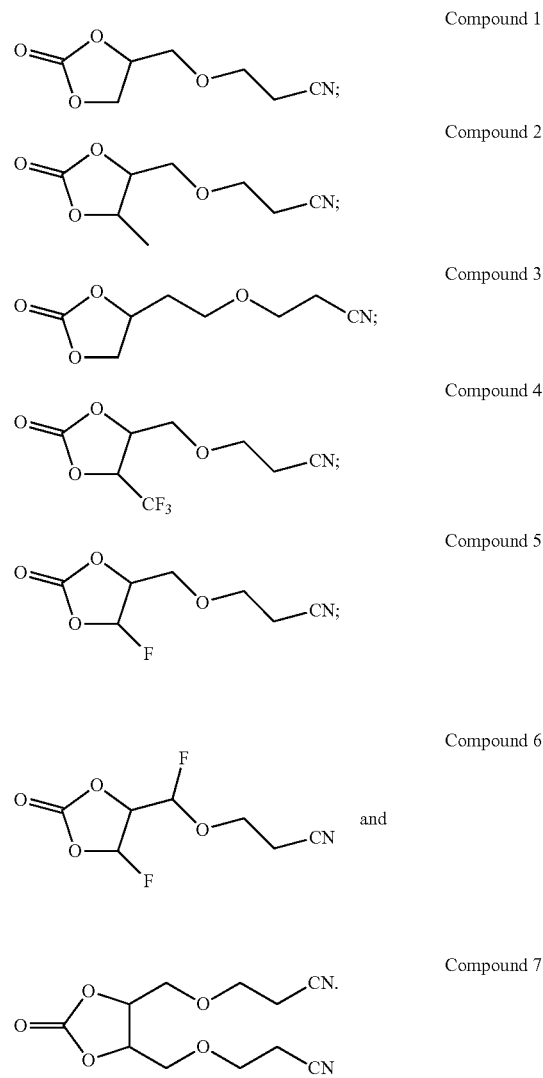

For the above compounds 1-7, those skilled in the art can deduce synthesis methods thereof according to their structural formulas and known knowledge. For example, the synthesis of compounds 1-4 is shown in the reaction formula (1), and the reaction steps are as follows: 1) under the action of an alkaline catalyst, the corresponding polyol and dimethyl carbonate undergo ester exchange reaction to obtain an alcohol ester intermediate after partial ester exchange; 2) the intermediate reacts with acrylonitrile or butenenitrile compound to obtain a crude product; 3) then the crude product is obtained after purification by column chromatography and the like.

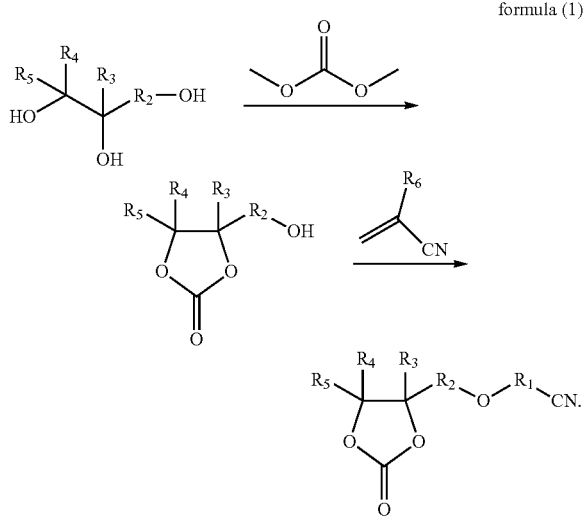

formula (1)

The synthesis of compounds 5-6 can be realized by reacting compound 1 with organic fluorinating agent Selectfluor™ to obtain a crude product, and then the crude product is purified by column chromatography, etc.

The non-aqueous electrolyte for lithium ion battery in the technical solution of the present application comprises at least one of unsaturated cyclic carbonate, fluorinated cyclic carbonate, cyclic sultones, cyclic sulfate, and nitriles. The unsaturated cyclic carbonate, fluorinated cyclic carbonate, cyclic sultones, cyclic sulfate, or nitrile compound can work together with the compound represented by formula I to form a passivation film on the surface of the electrode material, thereby further improving the stability of the electrode interface and further improving the performances of the battery.

Further, based on the total mass of the non-aqueous electrolyte for lithium ion battery being 100%, the percentage mass content of the unsaturated cyclic carbonate is 0.1-5%; the percentage mass content of the fluorinated cyclic carbonate is 0.1-80%; the percentage mass content of the cyclic sultones is 0.1-5%; the percentage mass content of the cyclic sulfate is 0.1-5%; the percentage mass content of the nitriles is 0.1-5%.

Preferably, the unsaturated cyclic carbonate further comprises at least one of vinylene carbonate, vinylethylene carbonate, and methylene vinyl carbonate;

Preferably, the fluorinated cyclic carbonate is at least one of fluoroethylene carbonate, trifluoromethyl vinyl carbonate and difluoroethylene carbonate;

Preferably, the cyclic sultones is at least one of 1,3-propane sultone, 1,4-butane sultone and propenyl-1,3-sultone.

Preferably, the cyclic sulfate is at least one of ethylene sulfate and 4-methyl vinyl sulfate;

Preferably, the nitriles are selected from at least one of succinonitrile (SN), adiponitrile (ADN), 1,2-bis (2-cyanoethoxy) ethane, 4-dicyano-2-butene, hexane-1,3,6-tricarbonitrile, and 1,2,3-tris (2-cyanoethoxy) propane.

The non-aqueous electrolyte for lithium ion battery of the present application contains solvent in addition to the above components. The solvent comprises at least one of cyclic carbonate, chain carbonate, fluorine-containing chain carbonate, carboxylic acid ester, fluorine-containing carboxylic acid ester and fluorine-containing aromatic hydrocarbon;

Preferably, the cyclic carbonate is selected from at least one of ethylene carbonate, propylene carbonate and butylene carbonate.

The chain carbonate is selected from at least one of dimethyl carbonate, diethyl carbonate, methyl ethyl carbonate and methyl propyl carbonate.

The fluorine-containing chain carbonate refers to a compound in which one or more hydrogen atoms in the chain carbonate are substituted with fluorine atoms.

The carboxylic acid ester is selected from at least one of methyl acetate, ethyl acetate, propyl acetate, methyl propionate, ethyl propionate and propyl propionate.

The fluorine-containing chain carbonate refers to a compound in which one or more hydrogen atoms in the chain carbonate are substituted with fluorine atoms.

The fluorine-containing aromatic hydrocarbon refers to a compound in which one or more hydrogen atoms in the aromatic hydrocarbon are substituted with fluorine atoms, for example, the fluorine-containing aromatic hydrocarbon is selected from benzene compounds substituted with one or more fluorines.

The addition amount of the above solvents can vary in a large range, specifically, it can be a general addition amount.

Further, the non-aqueous electrolyte for lithium ion battery of the present application contains lithium salt in addition to the above material components.

Preferably, the lithium salt is at least one of $LiPF_6$, $LiBF_4$, $LiN(SO_2CF_3)_2$, $LiN(SO_2C_2F_5)_2$, $LiC(SO_2CF_3)_3$ and $LiN(SO_2F)_2$.

The addition amount of the lithium salt can vary in a large range, specifically, it can be a general addition amount.

The non-aqueous electrolyte provided by the application contains the compound represented by formula I. When the non-aqueous electrolyte is used for lithium ion battery, the compound represented by structural formula I can undergo a reduction decomposition reaction prior to solvent molecules in the first charging process, and the reaction product forms a passivation film on the surface of the electrode, and the passivation film can inhibit further decomposition of solvent molecules and lithium salts. In addition, the compound represented by structural formula I can be complexed with high-valence metal ions on the surface of the positive electrode material, thus improving the stability of the surface of the positive electrode material and inhibiting the oxidative decomposition of electrolyte on the surface of the positive electrode, thereby greatly improving the high-temperature storage and high-temperature cycle performances of the battery.

On the premise of the non-aqueous electrolyte for lithium ion battery, the embodiment of the present application also provides a lithium ion battery.

In one embodiment, the lithium ion battery comprises a positive electrode, a negative electrode, a separator for separating the positive electrode and the negative electrode, and an electrolyte, wherein the electrolyte is the non-aqueous electrolyte as described above.

Specifically, the positive electrode comprises a positive electrode active material, and the active material of the positive electrode is at least one of $LiNi_xCo_yMn_zL_{(1-x-y-z)}O_2$, $LiCo_xL_{(1-x')}O_2$, $LiNi_{x'}L'_yMn_{(2-x''-y')}O_4$ and $Li_{z'}MPO_4$, wherein, L is at least one of Al, Sr, Mg, Ti, Ca, Zr, Zn, Si or Fe, $0 \le x \le 1$, $0 \le y \le 1$, $0 \le z \le 1$, $0 < x+y+z \le 1$, $0 < x' \le 1$, $0.3 \le x'' \le 0.6$, $0.01 \le y' \le 0.2$, L' is at least one of Co, Al, Sr, Mg, Ti, Ca, Zr, Zn, Si and Fe; $0.5 \le z' \le 1$, M is at least one of Fe, Mn and Co. The active material of the negative electrode is selected from artificial graphite and natural graphite. Obviously, it is not limited to the two listed.

The separator is a conventional diaphragm in the field of lithium ion batteries, and will not be further limited in the present application.

Because of the use of the non-aqueous electrolyte, the lithium ion battery provided by the embodiment of the present application can inhibit the decomposition of the electrolyte on the surfaces of positive and negative electrode materials, the performances of the lithium ion battery are greatly improved.

In order to better illustrate the technical solution of the present invention, the following description will be made with reference to specific embodiments.

Embodiment 1

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 1, based on the total mass of the non-aqueous electrolyte being 100%.

Embodiment 2

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 2, based on the total mass of the non-aqueous electrolyte being 100%.

Embodiment 3

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 3, based on the total mass of the non-aqueous electrolyte being 100%.

Embodiment 4

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 4, based on the total mass of the non-aqueous electrolyte being 100%.

Embodiment 5

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 5, based on the total mass of the non-aqueous electrolyte being 100%.

Embodiment 6

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 6, based on the total mass of the non-aqueous electrolyte being 100%.

Embodiment 7

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 7, based on the total mass of the non-aqueous electrolyte being 100%.

Embodiment 8

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 8, based on the total mass of the non-aqueous electrolyte being 100%.

Embodiment 9

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 9, based on the total mass of the non-aqueous electrolyte being 100%.

Embodiment 10

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 10, based on the total mass of the non-aqueous electrolyte being 100%.

Embodiment 11

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 11, based on the total mass of the non-aqueous electrolyte being 100%.

Embodiment 12

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 12, based on the total mass of the non-aqueous electrolyte being 100%.

Embodiment 13

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Embodiment 13, based on the total mass of the non-aqueous electrolyte being 100%.

Embodiment 14

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Embodiment 14, based on the total mass of the non-aqueous electrolyte being 100%.

Embodiment 15

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Embodiment 15, based on the total mass of the non-aqueous electrolyte being 100%.

Embodiment 16

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Embodiment 16, based on the total mass of the non-aqueous electrolyte being 100%.

Embodiment 17

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Embodiment 17, based on the total mass of the non-aqueous electrolyte being 100%.

Embodiment 18

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Embodiment 18, based on the total mass of the non-aqueous electrolyte being 100%.

Embodiment 19

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Embodiment 19, based on the total mass of the non-aqueous electrolyte being 100%.

Embodiment 20

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Embodiment 20, based on the total mass of the non-aqueous electrolyte being 100%.

Comparative Example 1

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Comparative Example 1, based on the total mass of the non-aqueous electrolyte being 100%.

Comparative Example 2

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Comparative Example 2, based on the total mass of the non-aqueous electrolyte being 100%.

Comparative Example 3

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Comparative Example 3, based on the total mass of the non-aqueous electrolyte being 100%.

Comparative Example 4

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Comparative Example 4, based on the total mass of the non-aqueous electrolyte being 100%.

Comparative Example 5

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Comparative Example 5, based on the total mass of the non-aqueous electrolyte being 100%.

Comparative Example 6

A 4.2V $LiNi_{0.5}Co_{0.2}Mn_{0.3}O_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 1, Comparative Example 6, based on the total mass of the non-aqueous electrolyte being 100%.

Comparative Example 7

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Comparative Example 7, based on the total mass of the non-aqueous electrolyte being 100%.

Comparative Example 8

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Comparative Example 8, based on the total mass of the non-aqueous electrolyte being 100%.

Comparative Example 9

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Comparative Example 9, based on the total mass of the non-aqueous electrolyte being 100%.

Comparative Example 10

A 4.4V $LiCoO_2$/artificial graphite battery, comprising a positive electrode, a negative electrode, a separator arranged between the positive electrode and the negative electrode, and an electrolyte, wherein the electrolyte is a non-aqueous electrolyte and comprises the following components in percentage by mass as shown in Table 2, Comparative Example 10, based on the total mass of the non-aqueous electrolyte being 100%.

In order to verify the influence of the non-aqueous electrolyte of the lithium ion battery of the present application on the battery performances, the lithium ion batteries prepared by the above Embodiments 1 to 20 and Comparative Examples 1 to 10 are subjected to performance tests below.

The tested performances include high-temperature cycle performance and high-temperature storage performance. The specific testing methods for each performance are as follows:

1. High-Temperature Cycle Performance Test

The lithium ion batteries prepared from Embodiments 1 to 20 and Comparative Examples 1 to 10 were placed in an oven at a constant temperature of 45° C., and charged to 4.2V($LiNi_{0.5}Co_{0.2}Mn_{0.3}O_2$/artificial graphite battery) or 4.4V($LiCoO_2$/artificial graphite battery) with 1C constant current, then charged till the current dropped to 0.02C at a constant voltage, and discharged to 3.0V with 1C constant current. In this cycle, the 1st discharge capacity and the last discharge capacity were recorded.

The calculation formula of high-temperature cycle capacity retention rate is as follows: Capacity retention rate=last discharge capacity/1st discharge capacity×100%

2. High-Temperature Storage Performance Test

The formed lithium ion battery was charged to 4.2V ($LiNi_{0.5}Co_{0.2}Mn_{0.3}O_2$/artificial graphite battery) or 4.4V($LiCoO_2$/artificial graphite battery) with 1C constant current/constant voltage at normal temperature. The initial discharge capacity and initial battery thickness of the battery were measured. Then the battery was stored at 60° C. for 30 days and discharged to 3V with 1C, the capacity retention, capacity recovery and battery thickness after stored were measured.

The calculation formula is as follows:

Battery capacity retention rate (%)=(retention capacity/initial capacity)×100%;

Battery capacity recovery rate (%)=(recovery capacity/initial capacity)×100%;

Battery thickness expansion rate (%)=(battery thickness after storage−initial battery thickness)/initial battery thickness×100%.

TABLE 1

Performances of the Batteries Made from the Non-aqueous Electrolytes by Embodiments 1 to 13 and Comparative Examples 1 to 6

| | | | | | After 30 days of storage at 60° C. | | |
|---|---|---|---|---|---|---|---|
| Embodiment | Positive electrode material | Compound represented by structural formula I and content | Other compounds and contents | The 500th cycle capacity retention rate at 45° C. 1 C | Capacity retention rate/% | Capacity recovery rate/% | Thickness expansion rate/% |
| Embodiment 1 | $LiNi_{0.5}Co_{0.2}Mn_{0.3}O_2$ | Compound 1: 1% | / | 80.3% | 80.3% | 83.6% | 10.8% |
| Embodiment 2 | $LiNi_{0.5}Co_{0.2}Mn_{0.3}O_2$ | Compound 2: 1% | / | 81.6% | 82.6% | 85.9% | 11.8% |
| Embodiment 3 | $LiNi_{0.5}Co_{0.2}Mn_{0.3}O_2$ | Compound 3: 1% | / | 80.9% | 80.5% | 84.5% | 12.9% |

TABLE 1-continued

Performances of the Batteries Made from the Non-aqueous Electrolytes by Embodiments 1 to 13 and Comparative Examples 1 to 6

|  |  |  |  |  | After 30 days of storage at 60° C. | | |
|---|---|---|---|---|---|---|---|
| Embodiment | Positive electrode material | Compound represented by structural formula I and content | Other compounds and contents | The 500th cycle capacity retention rate at 45° C. 1 C | Capacity retention rate/% | Capacity recovery rate/% | Thickness expansion rate/% |
| Embodiment 4 | $LiNi_{0.5}Co_{0.2}Mn_{0.3}O_2$ | Compound 5: 1% | / | 84.8% | 84.9% | 88.2% | 13.8% |
| Embodiment 5 | $LiNi_{0.5}Co_{0.2}Mn_{0.3}O_2$ | Compound 1: 0.1% | / | 72.5% | 71.1% | 74.7% | 20.6% |
| Embodiment 6 | $LiNi_{0.5}Co_{0.2}Mn_{0.3}O_2$ | Compound 1: 2% | / | 82.3% | 81.3% | 85.7% | 8.8% |
| Embodiment 7 | $LiNi_{0.5}Co_{0.2}Mn_{0.3}O_2$ | Compound 1: 3% | / | 84.3% | 83.3% | 87.7% | 8.8% |
| Embodiment 8 | $LiNi_{0.5}Co_{0.2}Mn_{0.3}O_2$ | Compound 1: 1% | VC: 1% | 84.1% | 83.4% | 87.6% | 15.8% |
| Embodiment 9 | $LiNi_{0.5}Co_{0.2}Mn_{0.3}O_2$ | Compound 1: 1% | FEC: 1% | 85.1% | 84.5% | 88.4% | 17.8% |
| Embodiment 10 | $LiNi_{0.5}Co_{0.2}Mn_{0.3}O_2$ | Compound 3: 3% | FEC: 5% | 85.1% | 84.5% | 88.4% | 17.8% |
| Embodiment 11 | $LiNi_{0.5}Co_{0.2}Mn_{0.3}O_2$ | Compound 1: 1% | PS: 1% | 82.2% | 85.8% | 89.7% | 7.8% |
| Embodiment 12 | $LiNi_{0.5}Co_{0.2}Mn_{0.3}O_2$ | Compound 1: 1% | DTD: 1% | 83.3% | 84.4% | 87.9% | 14.8% |
| Embodiment 13 | $LiNi_{0.5}Co_{0.2}Mn_{0.3}O_2$ | Compound 1: 1% | $LiN(SO_2F)_2$: 1% | 84.5% | 84.6% | 88.6% | 10.3% |
| Comparative Example 1 | $LiNi_{0.5}Co_{0.2}Mn_{0.3}O_2$ | / | / | 65.5% | 70.5% | 74.7% | 21.6% |
| Comparative Example 2 | $LiNi_{0.5}Co_{0.2}Mn_{0.3}O_2$ | / | VC: 1% | 78.2% | 77.1% | 80.7% | 24.1% |
| Comparative Example 3 | $LiNi_{0.5}Co_{0.2}Mn_{0.3}O_2$ | / | FEC: 1% | 76.5% | 75.5% | 78.7% | 28.4% |
| Comparative Example 4 | $LiNi_{0.5}Co_{0.2}Mn_{0.3}O_2$ | / | PS: 1% | 70.5% | 78.5% | 81.7% | 8.2% |
| Comparative Example 5 | $LiNi_{0.5}Co_{0.2}Mn_{0.3}O_2$ | / | DTD | 74.5% | 74.5% | 77.7% | 15% |
| Comparative Example 6 | $LiNi_{0.5}Co_{0.2}Mn_{0.3}O_2$ | / | $LiN(SO_2F)_2$: 1% | 72.5% | 76.5% | 80.7% | 15.7% |

Comparing Comparative Example 1 with Embodiments 1 to 4, it can be seen from the data in Table 1 that, respectively adding the Compound 1, Compound 2, Compound 3 or Compound 5 represented by structural formula I can greatly improve the high-temperature storage performance and high-temperature cycle performance of the battery.

Wherein, the capacity retention rate of the battery for the 500th cycle at 45° C. 1C increased from 65.5% to 80.3%, 81.6%, 80.9% and 84.8% respectively.

After storage at 60° C. for 30 days, the battery capacity retention rate increased from 70.5% to 80.3%, 82.6%, 80.5% and 84.9% respectively. The thickness expansion rate of the battery decreased from 21.6% to 10.8%, 11.8%, 12.9% and 13.8% respectively.

Comparing Embodiment 5 with Embodiment 1, Embodiments 6-7, it can be seen that, with the increase of the addition amount of Compound 1, the high-temperature storage performance and high-temperature cycle performance of the battery can be further improved.

Comparing the test results of Embodiments 8-13 with Comparative Examples 1 and Comparative Examples 2-6, it can be seen that, on the basis of compound 1 represented by structural formula I, adding conventional additives (VC, FEC, PS, DTD) or new lithium salt ($LiN(SO_2F)_2$) can also further improve the high-temperature storage performance and high-temperature cycle performance of the battery.

Therefore, the non-aqueous electrolyte for lithium ion battery provided by the present application can effectively improve the high-temperature storage performance and the high-temperature cycle performance of the lithium ion battery.

TABLE 2

Performances of the Batteries Made from the Non-aqueous Electrolytes by Embodiments 14 to 20 and Comparative Examples 7 to 10

|  |  |  |  |  | After 30 days of storage at 60° C. | | |
|---|---|---|---|---|---|---|---|
| Embodiment | Positive electrode material | Compound represented by structural formula I and content | Other compounds and contents | The 300th cycle capacity retention rate at 45° C. 1 C | Capacity retention rate/% | Capacity recovery rate/% | Thickness expansion rate/% |
| Embodiment 14 | $LiCoC_2$ | Compound 1: 1% | / | 70.4% | 72.1% | 77.5% | 15.5% |
| Embodiment 15 | $LiCoO_2$ | Compound 5: 1% | / | 72.1% | 73.5% | 78.7% | 16.7% |
| Embodiment 16 | $LiCoC_2$ | Compound 1: 1% | FEC: 1% | 75.4% | 75.8% | 80.1% | 20.2% |
| Embodiment 17 | $LiCoO_2$ | Compound 1: 3% | FEC: 5% | 80.4% | 76.8% | 82.3% | 15.8% |
| Embodiment 18 | $LiCoO_2$ | Compound 1: 3% | FEC: 5%, SN: 2% | 83.4% | 78.1% | 84.5% | 12.4% |
| Embodiment 19 | $LiCoO_2$ | Compound 1: 3% | FEC: 5%, PS: 3% | 85.8% | 81.2% | 86.4% | 10.4% |
| Embodiment 20 | $LiCoO_2$ | Compound 1: 3% | FEC: 5%, SN: 2%, ADN: 2% | 88.2% | 85.5% | 90.5% | 10.2% |
| Comparative Example 7 | $LiCoO_2$ | / | / | 60.1% | 62.5% | 66.7% | 25.5% |
| Comparative Example 8 | $LiCoO_2$ | / | FEC: 5%, SN: 2% | 70.2% | 70.1% | 84.5% | 20.1% |
| Comparative Example 9 | $LiCoO_2$ | / | FEC: 5%, PS: 3% | 75.4% | 75.4% | 79.4% | 17.2% |
| Comparative Example 10 | $LiCoO_2$ | / | FEC: 5%, SN: 2%, ADN: 2% | 65.4% | 77.4% | 81.4% | 15.2% |

Comparing Comparative Example 7 with Embodiments 7-14, it can be seen from the data in Table 2 that, respectively adding the Compound 1 and Compound 5 represented by structural formula I can greatly improve the high-temperature storage performance and high-temperature cycle performance of the battery.

Wherein, the capacity retention rate of the battery for the 300th cycle at 45° C. 1C increased from 60.1% to 70.4% and 72.1% respectively.

After storage at 60° C. for 30 days, the battery capacity retention rate increased from 62.5% to 72.1% and 73.5% respectively. The thickness expansion rate of the battery decreased from 25.5% to 15.5% and 16.7% respectively.

Comparing the test results of Embodiments 14 with Embodiments 16-20, it can be seen that, on the basis of compound 1 represented by structural formula I, adding conventional additives (FEC, PS, SN, ADN) can also further improve the high-temperature storage performance and high-temperature cycle performance of the battery.

The above descriptions are only preferred embodiments and are not intended to limit the present invention. Any modifications, equivalent substitutions and improvements made within the spirit and principles of the present invention shall be included within the scope of protection of the present invention. Further, unless otherwise required by context, singular terms shall include pluralities and plural terms shall include the singular. Thus, as used herein and in the claims, the singular forms include the plural reference and vice versa unless the context clearly indicates otherwise.

What is claimed is:

1. A non-aqueous electrolyte for lithium ion battery, comprising a compound represented by structural formula I:

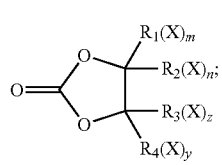

formula I in formula I, $R_1$, $R_2$, $R_3$ and $R_4$ are each independently selected from hydrogen atom, fluorine atom, cyano group, hydrocarbyl group or halogenated hydrocarbyl group having 1-5 carbon atoms, silicon-containing hydrocarbyl group having 1-5 carbon atoms, X is a —O—$R_5$—CN group, $R_5$ is a hydrocarbyl group or a halogenated hydrocarbyl group having 1-5 carbon atoms, m, n, z and y are integers of 0 or 1, and m+n+y+z≠0.

2. The non-aqueous electrolyte for lithium ion battery according to claim 1, wherein $R_1$, $R_2$, $R_3$ and $R_4$ are each independently selected from one of hydrogen atom, fluorine atom, cyano group, methyl group, ethyl group, propyl group, butyl group, fluorinated methyl group, fluorinated ethyl group, fluorinated propyl group, fluorinated butyl group, methylene group, ethylidene group, propylidene group, butylidene group, fluorinated methylene group, fluorinated ethylidene group, fluorinated propylidene group, and fluorinated butylidene group.

3. The non-aqueous electrolyte for lithium ion battery according to claim 1, wherein the compound represented by structural formula I is selected from the group consisting of:

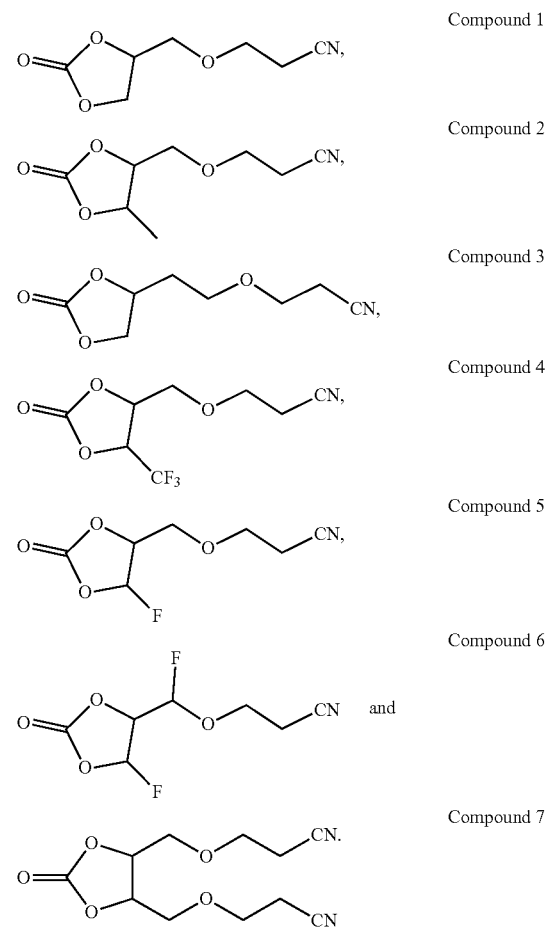

4. The non-aqueous electrolyte for lithium ion battery according to claim 1, wherein a percentage mass content of the compound represented by structural formula I is 0.1% to 10.0% based on a total mass of the non-aqueous electrolyte for lithium ion battery being 100%.

5. The non-aqueous electrolyte for lithium ion battery according to claim 1, wherein the non-aqueous electrolyte for lithium ion battery further comprises at least one of unsaturated cyclic carbonate, fluorinated cyclic carbonate, cyclic sultones, cyclic sulfate, and nitriles.

6. The non-aqueous electrolyte for lithium ion battery according to claim 5, wherein the unsaturated cyclic carbonate is at least one selected from vinylene carbonate, vinylethylene carbonate, and methylene vinyl carbonate;
   the fluorinated cyclic carbonate is at least one selected from fluoroethylene carbonate, trifluoromethyl vinyl carbonate and difluoroethylene carbonate;
   the cyclic sultones is at least one selected from 1,3-propane sultone, 1,4- butane sultone and propenyl-1,3-sultone;
   the cyclic sulfate is at least one selected from ethylene sulfate and 4- methyl vinyl sulfate;
   the nitriles are selected from at least one of succinonitrile, adiponitrile, 1,2-bis (2-cyanoethoxy) ethane, 1,4-dicyano-2-butene, hexane-1,3,6-tricarbonitrile, and 1,2,3-tris (2-cyanoethoxy) propane.

7. The non-aqueous electrolyte for lithium ion battery according to claim 5, wherein based on a total mass of the non-aqueous electrolyte for lithium ion battery being 100%, a percentage mass content of the unsaturated cyclic carbonate is 0.1-5%; a percentage mass content of the fluorinated cyclic carbonate is 0.1-80%; a percentage mass content of the cyclic sultones is 0.1-5%; the a percentage mass content of the unsaturated cyclic sulfate is 0.1-5%; the a percentage mass content of the nitriles is 0.1-5%.

8. The non-aqueous electrolyte for lithium ion battery according to claim 1, wherein the non-aqueous electrolyte for lithium ion battery comprises a solvent and a lithium salt;

the solvent comprises at least one of cyclic carbonate, chain carbonate, fluorine-containing chain carbonate, carboxylic acid ester, fluorine-containing carboxylic acid ester and fluorine-containing aromatic hydrocarbon;

the lithium salt is selected from at least one of $LiPF_6$, $LiBF_4$, $LiN(SO_2CF_3)_2$, $LiN(SO_2C_2F_5)_2$, $LiC(SO_2CF_3)_3$ and $LiN(SO_2F)_2$.

9. A lithium ion battery, comprising a positive electrode, a negative electrode, a separator for separating the positive electrode and the negative electrode, and an electrolyte, wherein the electrolyte is the non-aqueous electrolyte for lithium ion battery according to claim 1.

10. The lithium ion battery according to claim 9, wherein the positive electrode comprises a positive electrode active material, and the active material of the positive electrode is at least one of $LiNi_xCo_yMn_zL_{(1-x-y-z)}O_2$, $LiCo_xL_{(1-x)}O_2$, $LiNi_{x''}L'_{y'}Mn_{(2-x''-y')}O_4$ and $Li_zMPO_4$, wherein, L is at least one of Al, Sr, Mg, Ti, Ca, Zr, Zn, Si or Fe, $0 \le x \le 1$, $0 \le y \le 1$, $0 \le z \le 1$, $021\ x+y+z \le 1$, $0 < x' \le 1$, $0.3 \le x'' \le 0.6$, $0.01 \le y' \le 0.2$, L' is at least one of Co, Al, Sr, Mg, Ti, Ca, Zr, Zn, Si and Fe; $0.5 \le z' \le 1$, M is at least one of Fe, Mn and Co.

11. The non-aqueous electrolyte for lithium ion battery according to claim 8, wherein the cyclic carbonate is selected from at least one of ethylene carbonate, propylene carbonate and butylene carbonate; the chain carbonate is selected from at least one of dimethyl carbonate, diethyl carbonate, methyl ethyl carbonate and methyl propyl carbonate; the carboxylic acid ester is selected from at least one of methyl acetate, ethyl acetate, propyl acetate, methyl propionate, ethyl propionate and propyl propionate; the fluorine-containing aromatic hydrocarbon is selected from at least one of benzene compounds substituted with one or more fluorines.

* * * * *